(12) United States Patent
Kastrup et al.

(10) Patent No.: US 8,755,116 B2
(45) Date of Patent: Jun. 17, 2014

(54) WAVELENGTH OR POLARIZATION SENSITIVE OPTICAL ASSEMBLY AND USE THEREOF

(75) Inventors: Lars Kastrup, Göttingen (DE); Volker Westphal, Hannover (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 525 days.

(21) Appl. No.: 12/628,408

(22) Filed: Dec. 1, 2009

(65) Prior Publication Data

US 2010/0142054 A1    Jun. 10, 2010

Related U.S. Application Data

(63) Continuation-in-part of application No. PCT/EP2008/004291, filed on May 30, 2008.

(51) Int. Cl.
  *G02B 5/30* (2006.01)
  *G02B 27/00* (2006.01)
  *G02B 27/28* (2006.01)

(52) U.S. Cl.
  USPC ............. 359/489.01; 359/489.07; 359/577; 359/579; 359/615; 385/32

(58) Field of Classification Search
  USPC ........... 359/279, 371, 489.07, 565, 615, 724, 359/245, 489.01, 577, 579; 362/290; 385/28, 32
  See application file for complete search history.

(56) References Cited

U.S. PATENT DOCUMENTS 2,553,108 A * 5/1951 Osterberg et al. ............. 359/370
2,687,670 A * 8/1954 Locquin ........................ 359/370
(Continued)

FOREIGN PATENT DOCUMENTS

DE   100 12 462 A1   9/2001
DE   101 54 699 A1   5/2003
(Continued)

OTHER PUBLICATIONS

Japanese Office Action in co-pending, related JP No. 2010-509735, mailed Sep. 18, 2012. (English Translation also attached).

(Continued)

*Primary Examiner* — Ricky D Shafer
(74) *Attorney, Agent, or Firm* — Thomas | Horstemeyer, LLP

(57) ABSTRACT

In an optical assembly having a light source which provides two optically different light components with essentially planar wavefronts on an optical axis, wherein the light components differ at least in their wavelength; in the case of an objective lens which projects the two optically different light components into a projection space; and in the case of an optical component which is arranged on the optical axis and has an plane through which the wavefronts of the two light components pass and in which at least two different areas of the optical component with different dispersion behaviors $n(\lambda)$ abut against one another in the lateral direction with respect to the optical axis; the optical component causes phase shifts of the wavefronts of the two light components, wherein the phase shift of the wavefronts of the one light component differs by at least one quarter of the wavelength of that light component between the two different areas, and wherein the phase shift of the wavefronts of the other light component does not differ between the two different areas, such that an intensity distribution of the one light component in the projection space by interference with itself differs from an intensity distribution of the other light component in the projection space.

27 Claims, 3 Drawing Sheets

(56) References Cited

U.S. PATENT DOCUMENTS

| | | | |
|---|---|---|---|
| 2,821,108 A * | 1/1958 | Warmisham et al. | 359/724 |
| 3,628,848 A * | 12/1971 | Nomarski | 359/371 |
| 4,896,967 A * | 1/1990 | Douglas-Hamilton et al. | 382/128 |
| 5,113,285 A * | 5/1992 | Franklin et al. | 359/465 |
| 5,349,592 A * | 9/1994 | Ando | 372/32 |
| 5,420,717 A * | 5/1995 | Tabata | 359/371 |
| 5,604,591 A * | 2/1997 | Kitagawa | 356/491 |
| 5,739,952 A * | 4/1998 | Takeda et al. | 359/489.06 |
| 5,973,785 A * | 10/1999 | Okamoto | 356/521 |
| 6,259,104 B1 | 7/2001 | Baer | |
| 6,292,287 B1 | 9/2001 | Fujinoki | |
| 6,646,281 B1 * | 11/2003 | Krantz et al. | 250/559.45 |
| 2001/0042837 A1 | 11/2001 | Hoffmann | |
| 2006/0007535 A1 | 1/2006 | Gugel | |
| 2008/0007735 A1 | 1/2008 | Hell et al. | |

FOREIGN PATENT DOCUMENTS

| | | |
|---|---|---|
| DE | 103 13 138 A1 | 10/2004 |
| DE | 10 2004 032 953 A1 | 2/2006 |
| DE | 10 2005 013 116 A1 | 10/2006 |
| DE | 10 2005 013 969 A1 | 10/2006 |
| DE | 10 2005 020 003 A1 | 11/2006 |
| DE | 10 2006 011 556 A1 | 3/2007 |
| EP | 1 662 296 A1 | 5/2006 |
| JP | 2000-329690 A | 11/2000 |
| JP | 2003-167198 A | 6/2003 |
| JP | 2006-058477 A | 3/2006 |
| WO | 2006078857 A2 | 7/2006 |

OTHER PUBLICATIONS

Klar, T. et al.: "Fluorescence Microscopy With Diffraction Resolutin Barrier Broken by Stimulated Emission" In: Proceedings of the National Academy of Sciences of USA, National Academy of Science, Washington, DC. vol. 97, No. 15; Jul. 18, 2000, pp. 8206-8210.

Klar, T. et al.: "Breaking Abbe's Diffracion Resolution Limit in Fluorescence Microcopy with Stimulated Emission Depletion beams of Various Shapes." In: Physical Review E. Statistical Physics, Plasmas, Fluids, Andrelated Interdisciplinary Topics; American Institute of Physics, New York. vol. 64, No. 6, Jan. 1, 2001, pp. 66613/1-66613/9.

Westphal, V. et al.: "Lateral Resolution of 28 nm (Lambda/25) in Far-Field Fluorescence Microscopy." Applied Physics B. vol. 77, 2003, pp. 377-380.

Westphal, V. et al.: "Laser-Diode-Stimulated Emission Depletion Microscopy," in: Applied Physics Letter AIP, American Institute of Physics, Melville, NY. vol. 62, No. 183, May 5, 2003, pp. 3125-3127.

Bossi, Mariano et al.: "Breaking The Diffraction Resolution Barrier in Far-Fieid Microscopy by Molecular Optical Bistability." in: New Journal of Physics, Institute of Physics Publishing, Bristol, GB. vol. 8, No. 11; Nov. 1, 2006, pp. 275-275.

PCT International Search Report and Written Opinion on related, co-pending PCT Application No. PCT/2008/004291, Issued Dec. 7, 2009.

* cited by examiner

WAVELENGTH OR POLARIZATION SENSITIVE OPTICAL ASSEMBLY AND USE THEREOF

CROSS-REFERENCE TO RELATED APPLICATIONS

This application is a Continuation in Part of international patent application PCT/EP2008/004291, entitled "Wavelength-sensitive or polarization-sensitive optical assembly and use thereof", filed on May 30, 2008 and claiming the priority of the parallel-attached German patent application No. DE 10 2007 025 688.6 entitled "Wavelength-sensitive or polarization-sensitive optical assembly and use thereof", filed on Jun. 1, 2007.

FIELD OF THE INVENTION

The invention relates to an optical assembly, and in particular the invention relates to an optical assembly having a light source which provides two optically different light components with essentially planar wavefronts on an optical axis, wherein the light components differ at least in their wavelength, and having an objective which projects the two optically different light components into a projection space. The optical assembly is intended in particular for use in fluorescence light microscopy. The invention also relates to an optical component which is particularly suitable for an optical assembly such as this, but which also has other uses.

BACKGROUND TO THE INVENTION

It is known in so-called STED fluorescence optical microscopy for a sample which has first of all been excited to fluoresce by means of excitation light to be deexcited again with deexcitation light down to a spatially tightly bounded area before the detection of fluorescence light which is emitted spontaneously from the sample. If this area is the null of an interference pattern of the deexcitation light and the intensity of the deexcitation light is high, it is possible to reduce the spatial dimensions of this area from which the spontaneously emitted fluorescence light can exclusively originate below the diffraction limit for the wavelength of the light being used. This results in a considerable increase in the spatial resolution for imaging of the sample by means of the spontaneously emitted fluorescence light.

The interference pattern of the deexcitation light is frequently produced with the aid of a phase filter or spatial light modulator, by means of which incident planar phase fronts of the deexcitation light are deliberately deformed. For example, the phase fronts can thus be delayed in a central area close to the optical axis, in comparison to the phase fronts in the periphery. During focusing of the deexcitation light, this results in an interference pattern with a null at the focus point, which null, in the direction of the optical axis, lies between two main maxima of the light intensity distribution and on the focal plane within a ring of weak intensity. Another doughnut-shaped interference pattern with a null line along the optical axis through the focus point can be achieved by providing the incident planar wavefronts of the deexcitation light with a phase delay which rises in a helical shape about the optical axis up to a wavelength of the deexcitation light.

In known STED microscopes, the deexcitation light whose phase fronts have been distorted in this way is combined with the excitation light and is directed into an objective lens which focuses both the excitation light and the deexcitation light into the respective sample and also receives fluorescence light coming from the sample (see for example the published German patent application DE 10 2005 020 003 A1). The fluorescence light from the sample can in this case pass back in a known manner essentially on the same path as that over which the excitation light previously passed. The excitation light can thus pass through a pinhole in order to image a point light source in the sample by means of the objective lens, and the fluorescence light from the sample can pass back through a conjugate pinhole, after separation of the excitation light by means of a wavelength-selective beam splitter, thus resulting in a so-called confocal arrangement. One advantage in this case is that all the changes to the optical assembly between the pinhole and the sample affects the excitation light and the fluorescence light in the same way. However, this involves major adjustment effort, in order to coaxially align the beam paths of the excitation light on the one hand and of the deexcitation light on the other hand accurately with respect to one another.

A similar problem occurs in RESOLFT fluorescence optical microscopy, in which the basic state of a fluorescent dye in a sample is first of all depopulated with depopulation light down to a spatially closely confined area before the sample is excited to fluoresce by means of excitation light, in order to detect fluorescence light from the sample. When the spatially closely confined area is the null of an interference pattern of the depopulation light, and the intensity of the depopulation light is high, it is possible to reduce the spatial dimensions of this area, from which the fluorescence light can exclusively originate, below the diffraction limit at the wavelength of the light being used. In this case, this also means a considerable increase in the spatial resolution for imaging of the sample by the fluorescence light. In RESOLFT fluorescence light microscopy, the depopulation light and the excitation light, which may be at the same wavelength, can be combined onto a common optical axis.

In addition to the already mentioned spatial light modulator, the described aberrations of planar wavefronts of the deexcitation light can be effected by phase filters (see for example DE 10 2006 011 556 A1), phase delay elements, e.g. deposited onto a plane-parallel glass plate, or can be produced by a stepped glass plate or a helical glass plate, which is referred to as a phase clock.

Although the use of so-called spatial light modulators is advantageous to the extent that fronts of any desired shape can in theory be generated; it is found, however, that the beam quality is adversely affected by spatial light modulators independently of the applied modulation of the phase shift.

In the case of optical components with phase delay elements and/or stepped or helical thickness, no adverse effect on the deexcitation light passing through can admittedly be expected, apart from the desired variation of the phase fronts, but these components are only suitable for deexcitation light in a narrow wavelength range.

This also applies to a phase filter which applies to linear phase ramps in opposite senses to the light passing through, and which is known from G.-H. Kim, J.-H. Jeon, K.-H. Ko, H.-J. Moon, J.-H. Lee and J.-S. Chang, "Optical vortices produced with a nonspiral phase plate", *Appl. Opt.* 36, 8614-8621 (1997).

EP 1 662 296 A1 describes an optical assembly having the features of the preamble of patent claim 1, in which the two light components have different polarization such that the wavefronts of the one light component are deformed by a spatial light modulator, while the wavefronts of the other light component pass through a spatial light modulator without being deformed. The beam paths of the two light components, for example of the excitation light and of the deexcitation light in the case of a STED fluorescence optical microscope, therefore need not be separated. The known adverse effects on the beam quality caused by a spatial light modulator occur in both light components in this case, however.

There is therefore still a requirement for an optical assembly in which, for example, the adjustment effort for the combination of the deexcitation light and of the excitation light in an STED fluorescence optical microscope or the depopulation light and the excitation light in an RESOLFT fluorescence optical microscope can be reduced considerably without any adverse effects on the beam quality.

SUMMARY OF THE INVENTION

In one aspect, the invention provides an optical assembly which comprises a light source, which provides two optically different light components with essentially planar wavefronts on an optical axis, wherein the light components differ at least in their wavelength, an objective lens which projects the two optically different light components into a projection space, and an optical component. The optical component in this optical assembly is arranged on the optical axis and has an aperture, through which the wavefronts of the two light components pass and, in mutually adjacent areas of the aperture, has a different design along the optical axis with a different dispersion behavior $n(\lambda)$, wherein the optical component causes phase shift of the wavefronts of both light components, wherein the phase shifts of the wavefronts of one light component has at least one step of at least one quarter of the wavelength of that light component between the mutually adjacent areas of the aperture of different design, and wherein the phase shift of the wavefronts of the other light component is constant across the aperture as it passes through the component, such that an intensity distribution of the one light component in the projection space by mutual interference differs from an intensity distribution of the other light component in the projection space.

In a more detailed aspect, the invention provides an optical assembly which has a light source, which provides two optically different light components with essentially planar wavefronts on an optical axis, wherein the light components differ at least in their wavelength; an objective lens, which focuses the two optically different light components into a focus area; and an optical component, which is arranged on the optical axis and has an aperture, through which the wavefronts of the two light components pass and, in mutually adjacent areas of the aperture, has a different design along the optical axis with a different dispersion behavior $n(\lambda)$, wherein the optical component causes phase shifts of the wavefronts of both light components, wherein the phase shift of the wavefronts of one light component has at least one step of at least 50% of the wavelength of that light component between the mutually adjacent areas of the aperture of different design, and wherein the phase shift of the wavefronts of the other light component is constant across the aperture as it passes through the component, and wherein the optical component varies the phase shift of the wavefronts of the one light component over the aperture such that the intensity distribution of that light component has a null at the center of the focus area, at which the intensity distribution of the other light component is concentrated.

In a further aspect, the invention provides an optical component having at least one solid body which provides different optical path lengths parallel to an optical axis in different areas for light at least one wavelength, and having at least one molding, which is connected to the solid body in at least one of the areas along the optical axis, wherein a refractive index difference between the solid body and the molding can be adapted to different wavelengths such that a predetermined difference of at least one quarter of the respective wavelength can be set exactly for the optical path lengths in the different areas.

BRIEF DESCRIPTION OF THE FIGURES

The invention will be understood better if the following drawings are considered. The parts in the drawings are not necessarily shown to scale, and instead of this value is placed on clearly illustrating the principles of the present invention. The same reference symbols in the drawings denote the same parts in the various views.

DETAILED DESCRIPTION

Figure 1:
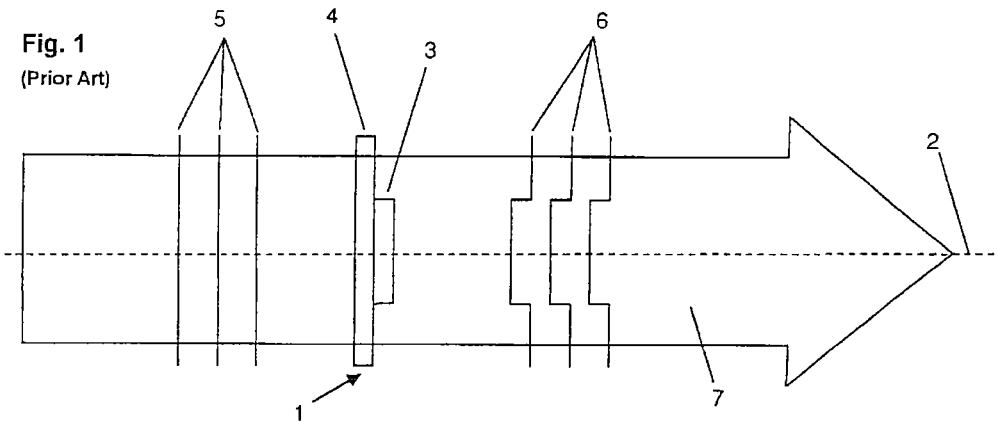
FIG. 1 shows the basic principle of a phase filter as is already known in the prior art.

The patent claims and the following description refer only to two optically different light components, and this does not preclude the optional occurrence of further light components. The expression a light component means not only exclusively strictly monochromatic light; a light component may also cover a certain wavelength range.

In the novel optical assembly, two different light components pass through an optical component, wherein the optical component deforms the wavefronts of the one light component such that the intensity distribution of that light component in a projection space differs by interference with itself from the intensity distribution of the other light component in the projection space. Specifically, for this purpose, the optical component is phase-corrected for the other light component. At the least, phase correction is possible for example by varying the refractive index associated with the other light component of a part of the optical component.

Since the beam paths of both light components extend through the optical component, both light components can be passed coaxially over a large proportion of the optical assembly, which means that relative adjustment of their beam paths is not necessary, at least over this part of the optical assembly. Changes to this part of the optical assembly affect both light components in the same way. The only difference for the two light components is that the wavefronts of the one light component are deformed by the optical component, while this deformation does not occur for the other light component, even though its beam path likewise passes through the optical component, and that the intensity distribution of the one light component has a null in the center of the focus area of the objective lens that follows the optical component, in which the intensity distribution of the other light component is concentrated, because of the deformation of their wavefronts. The null may in this case be a null point or else a null line which typically runs in the direction of the optical axis, or may be a null plane. The above definition of the present invention as can be seen, goes further than its application option to the field of STED fluorescence optical microscopy. The optical assembly according to the invention can therefore also be used in other technical fields, for example for optical pincettes for picking up particles and their manipulation with light or else for optical atom traps.

By way of example, when using the optical assembly in fluorescence optical microscopy, it is possible for the beam path of light detected by the objective lens from the focus area, that is to say in particular fluorescence light, to also pass through the optical component. In this case, the optical component may also be phase-corrected for this light, or at least may be phase-correctable. However, this is not absolutely essential since a phase error in the light passing through the optical component, for example in the case of confocal detection of fluorescence light, means only a loss of intensity, which remains correspondingly small for small phase errors.

In order to input the beam paths of the one light component and of the other light component coming from different light sources coaxially into the novel optical assembly, a common optical waveguide can be provided. This should be chosen such that it itself does not lead to disturbing aberrations of the wavefronts. A single-mode fiber is highly suitable as an optical waveguide. The optical waveguide ideally has the single-mode characteristic both for the one light component and for the other. The single-mode characteristic is particularly important with respect to the one light component whose phase fronts are intended to be deliberately deformed by the optical component. Furthermore, the single-mode fiber preferably maintains the polarization of the light components passed by it. A person skilled in the art knows that the polarization-maintaining characteristic of the single-mode fiber is a precondition for the operation of some embodiments of the present invention which uses a single-mode fiber.

If the two light components have greater differences between the wavelengths, it may be difficult to find a fiber as an optical waveguide for this purpose which is a single-mode fiber for both wavelengths. However, it is not just then that it is possible to focus both light components through the opening of a pinhole which is located at the focal point of a lens arranged on the other side of the pinhole. The lens forms wavefronts from the light emerging from the pinhole, which wavefronts are very largely oriented at right angles to the optical axis. Deviations which occur in this case from the ideally planar wavefronts remain irrelevant as long as the angle between the beam paths of the two light components in front of the pinhole remains small.

The assembly explained above with reference to examples with an optical waveguide and a pinhole, for coaxially inputting the two light components into the novel optical assembly is in general referred to as a spatial filter and can be designed in a manner which is known in principle for a spatial filter to a person skilled in the art.

For example, when the novel optical assembly is used in fluorescence optical microscopy, the beam path of light which is detected by the objective lens from the focus area, that is to say in particular fluorescence light, will likewise pass through the optical waveguide and/or the pinhole, in which case a detector for the fluorescence light is then arranged behind the optical waveguide or the pinhole, in the same way as the light sources for the two light components.

In the novel optical assembly, the optical component has at least one step over its active surface, of at least one quarter, and preferably of at least 50%, of the wavelength of the one light component in the phase shift which it applies to the one light component, with the phase shift which the optical component applies to the other light component being set, or having the capability to be set, such that it does not change over the step. Relatively minor changes in the phase shift which the optical component also applies to the other light component are invariably feasible and permissible within the scope of the invention. By way of example, the optical component can apply the same basic phase shift to both light components. However, in this case, the phase shift which is applied to the one light component additionally has the step over at least one direction which runs transversely, that is to say for example at right angles, to the optical axis of the optical component. Within the scope of the present invention, it is also permissible for the other light component likewise to be provided with a phase shift with a step by the optical component, if this step is considerably smaller, that is to say at most half the size, at preferably a maximum of 20%, and most preferably a maximum of 10%, of the size of the step which is applied to the one light component. Furthermore, relative phase shifts between the two light components or else over the wavefront of one of the light components are insignificant, provided that they are an integer multiple of the wavelength of the respective light. The expression a step in the phase shift should be understood as meaning not only what is covered exactly by a discontinuity on the basis of the mathematical definition but also everything which does not differ in its practical optical effects during use of the novel optical assembly. By way of example, the step may comprise a flank with a limited phase shift gradient, and/or may have rounded edges on the phase shift.

The novel optical component preferably has a step of at least one quarter of the wavelength in the phase shift which it applies to the light component in every direction running at right angles to its optical axis. The phase shifts of the other light component over these directions are in each case at least considerably smaller, if they are present at all.

In one specific embodiment of the optical component, the aperture of the optical component may, for example, have a circular central area and a periphery which extends in an annular shape around it, between which the difference in the phase shift of the one light component is 50% of its wavelength.

In another specific embodiment, the optical component applies a phase-shift difference to the one light component, which difference increases in the circumferential direction about its optical axis up to its wavelength. In this case, the step in the phase shift is located along every direction which runs at right angles to the optical axis over the aperture.

In a further embodiment, the optical component applies phase shifts from 0 to 50% and from 50% to 100% of the wavelength of the one light component, to that light component, along two linear ramps which are parallel but have opposite gradients. In this case, the step in the phase shift is located, for example, along the direction which runs over the aperture at right angles to the optical axis and at right angles to the two ramps.

In the case of the optical component, two areas with a different dispersion behavior $n(\lambda)$ are adjacent to one another at the step in the phase shift. The two mutually adjacent areas provide different optical path lengths for the one light component and the same optical path lengths for the other light component.

In this case, not only may the mutually adjacent areas with a different design each be bounded by plane-parallel surfaces in the direction of the optical axis of the optical component, but the entire optical component may also be bounded by two parallel surfaces in the direction of its optical axis.

Specifically, the optical component may have different materials or different material combinations in its different areas. As a preferred embodiment, this also includes the mutually adjacent areas with a different design being provided with the same materials in different thicknesses.

One particularly preferred embodiment of the novel component consists in two areas which are mutually adjacent transversely with respect to the optical axis, each composed of optical wedges which are cemented or spread to be plane-parallel, composed of at least two different optical materials which are chosen such that the wavefront of the one light component remains unchanged when it passes through the optical component, while the wavefront of the other light component has applied to it two parallel linear phase ramps with gradients in opposite senses.

One of the materials of the optical component may have a variable dispersion behavior $n(\lambda)$ in order to match the optical component to the light at the one and/or at the other wavelength. For this purpose, at least one of the materials of the optical component may have a temperature-dependent dispersion behavior $n(\lambda, T)$, wherein a temperature control apparatus is associated with this material, or at least one of the materials may have electrically variable dispersion characteristics $n(\lambda, U)$ wherein an electrode to which a voltage U can be applied is associated with this material. Furthermore, the dispersion behavior of the at least one material may be variable by means of a magnetic field ($n(\lambda, B)$) or through the concentration of at least one component of the material ($n(\lambda, c)$).

It is particularly advantageous for the refractive index difference between the solid body and the molding to be variable such that it results in a difference in the optical wavelengths of at least one quarter, and preferably of at least half, the wavelength of the one light component for that light component, while the difference for the optical wavelengths for another light component with different optical characteristics is zero.

In particular, gels, immersion oils, dye solutions and liquid crystals may be used as a material with highly pronounced dispersion $n(\lambda)$ which, for example, is suitable for designing the novel optical component, in combination with a solid body composed of a material whose dispersion behavior is less pronounced.

In one embodiment of the optical component, a cuvette is provided, in which the depth of its interior in the direction of the optical axis of the optical component varies over a direction which runs at right angles to its optical axis. A fluid medium may be introduced into the interior in the cuvette which, together with the solid body of the cuvette, which may be bounded on the outside by plane-parallel surfaces, provides the desired optical characteristics for the optical component.

Both the wavelengths and the polarizations of the two light components may differ in the optical assembly. This makes it possible to provide a defined step in the phase shift for a certain wavelength range of the one light component, and no step in the phase shift for a certain wavelength range of the other light component, for example by using a birefringent material in the optical component. By way of example, the one light component may comprise, for example, excitation light at various wavelengths within a first wavelength window, while the other light component may comprise deexcitation light at various wavelengths within a second wavelength window.

An optical component as is preferably used for the novel optical assembly may also advantageously be used for light at only one wavelength. The special feature therein is that at least one molding is connected along the optical axis in at least one of the areas to a solid body which provides different optical path lengths parallel to the optical axis of the component, in different areas of the optical component, for light at least one wavelength, wherein a refractive index difference between the solid body and the molding is variable in order to vary the optical path lengths which differ because of the solid body. The optical component can therefore be adapted overall to the wavelength of the light for which it is currently being used. Specifically, for example, a step in the optical path length, which the optical component applies to planar phase fronts, can be matched exactly to half the wavelength of the light.

Furthermore, an optical component as is preferably used for the novel optical assembly can be used and modified such that it also deforms the wavefronts of the other light component, to be precise with the opposite mathematical sign to the deformations of the one light component. In this case, it is particularly preferable for the magnitudes of the deformations of both light components to be of the same magnitude with respect to the respective wavelength. A material with a pronounced dispersion behavior $n(\lambda)$ can be chosen for this purpose, for example, in which, in comparison to the refractive index n of another material in the optical component with a less pronounced dispersion behavior, this results in a positive refractive index difference $\Delta n$ for the one light component, and at the same time in a negative refractive index difference $-\Delta n$ for the other light component, or vice versa.

Referring now in more detail to the drawings, FIG. 1 shows an optical component or phase filter 1 which has a phase delay element 3 on a glass substrate 4 in the area of its optical axis 2. In the central area of the phase filter 1 with respect to the periphery of the phase filter 1, the phase delay element 3 ensures a delay of planar wavefronts 5 which are incident in the direction of the optical axis 2, as is sketched for the modified wavefronts 6. In this case, the relative phase delay of the modified wavefronts 6 in the central area of the phase filter 1 corresponds to half the wavelength of the light 7 under consideration here. If the modified wavefronts 6 are focused by means of an objective lens at a focus point, a null of the intensity distribution of the light 7 is formed by interference effects on the focus point itself, which is enclosed between two main maxima of the intensity distribution in the direction of the optical axis 2 and is surrounded on the focal plane by a ring in which the interference pattern has a weak intensity. The phase filter 1 as shown in FIG. 1 modifies incident wavefronts at any wavelength. In the case of a wavelength to which the phase delay element 3 is not matched, the relative delay of the wavefronts in the central area of the phase filter 1 is, however, not half a wavelength but a delay value which is dependent on the wavelength of the light which is then under consideration. The specific phase shift depends on the different, optical path lengths parallel to the optical axis 2 through the phase delay element 3, and through the air which radially surrounds it. The substrate 4, which has plane-parallel boundaries, only ensures a phase delay which is uniform over the entire cross section of the light 7, that is to say that there is no relative phase delay over the individual wavefronts.

Figure 2:
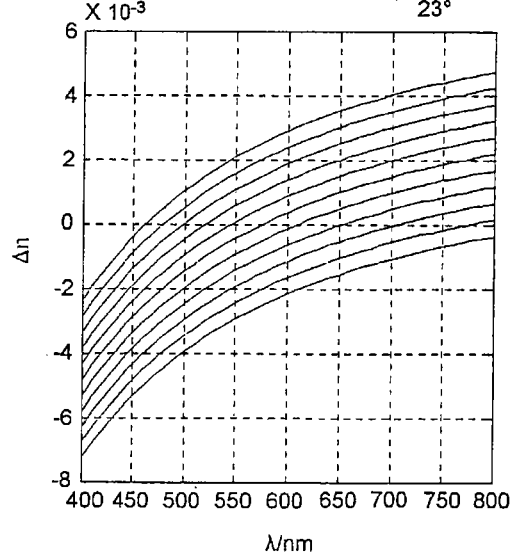
FIG. 2 shows dispersion curves for the combination of a glass substrate (BK7) with a mixture of two immersion oils (Cargille Type B and Cargille Type 37) as an adjacent medium. Different mixture ratios of the two oils are plotted on the left in FIG. 2, with the proportion of the Type B oil rising from the bottom upward, while the dispersion curves for a 1:1 mixture are plotted on the right-hand side, for temperatures rising from the bottom upward.
Figure 2:
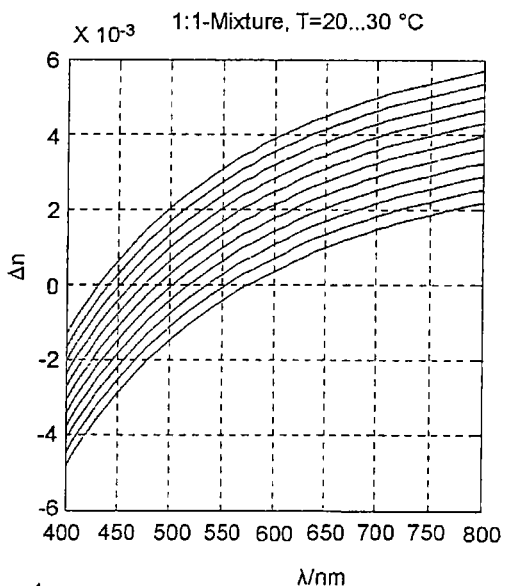
Figure 3:
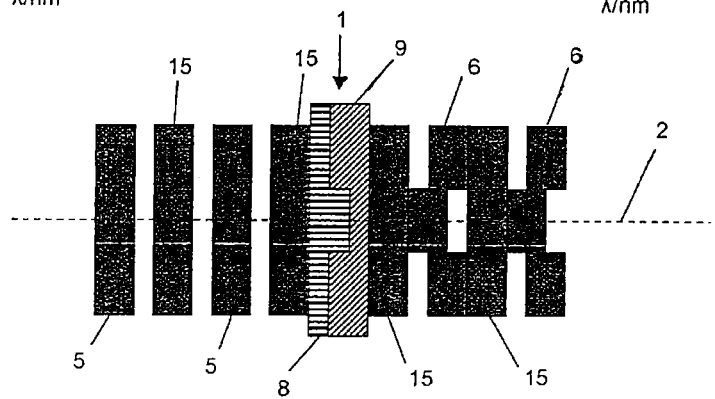
FIG. 3 shows the effect of a wavelength-selective phase filter on planar wavefronts of light at a different wavelength.

In conjunction with FIG. 2, FIG. 3 shows the capability of designing the phase filter 1 such that it distorts incident planar wavefronts 5 at a first wavelength corresponding to FIG. 1 into modified wavefronts 6, while incident planar wavefronts 15 at a different wavelength pass through the phase filter 1 without being deformed. In this case, the phase filter 1 is based on two materials 8 and 9, which are arranged one behind the other along the optical axis 2. The combination of the two materials 8 and 9, that is to say the entire phase filter 1, is bounded in a plane-parallel form; the extent of the material 8 in the central area of the phase filter 1 close to the optical axis 2 is, however, greater than in its periphery. The extent of the material 9 parallel to the optical axis 2 in this central area is correspondingly less than in the periphery. The differences between the extents of the two materials 8 and 9 along the optical axis 2 are matched to a dispersion behavior $n(\lambda)$ of the material 9 such that this results in the phase delay of $\lambda/2$ in the central area of the phase filter 1 when the wavefronts 5 have the wavelength $\lambda$. At the same time, the dispersion behavior $n(\lambda)$ of the material 9 is, however, also matched to the material 8 such that the refractive indices n of both materials 8 and 9 are the same for the light of the wavefronts 15 at a different wavelength.

Specifically, the material 9 may, for example, be an immersion oil, whose composition or temperature is matched on the basis of the dispersion curves shown in FIG. 2 such that it has a $\Delta n$ value of zero for the wavelength $\lambda$ of the wavefronts 15, with respect to the material 8. For the wavelength of the wavefronts 5, the $\Delta n$ value must be positive, in order to produce the delay of the wavefronts 6 as shown in FIG. 3 in the central area of the phase filter 1. The magnitude of the delay may in this case be set both by the $\Delta n$ value and by the difference in the extent of the two materials 8 and 9 between the central area and the periphery. In principle, the $\Delta n$ value for the wavelength of the wavefronts 5 may also be negative, in which case the wavefronts 6 are then deformed in the opposite manner, that is to say they are delayed in their periphery in comparison to their centre.

Figure 4:
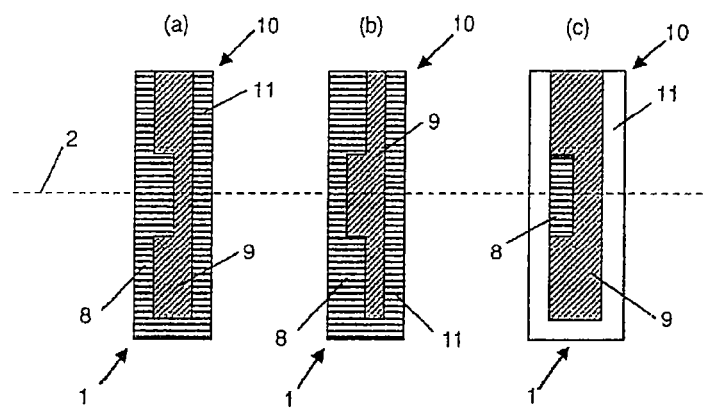
FIG. 4 shows three specific embodiments of a wavelength-selective phase filter based on a cuvette with a front face which is stepped in the direction of the optical axis.

A cuvette 10 can be provided for the material 9 in the form of an immersion oil, three embodiments of which are shown in FIG. 4 and whose interior in the direction of the optical axis 3 has a depth which has a step over a direction at right angles to the optical axis. In this case, the cuvette 10 in FIG. 4(a) corresponds to the phase filter 1 shown in FIG. 3, in which the material 8 has the greater axial extent in the central area of the phase filter 1. The cuvette 10 shown in FIG. 4(b) illustrates the opposite situation. The material 9 for filling the cuvette 10 may be not only a dispersion oil but also any other fluid material, for example a liquid polymer, a liquid crystal or a dye solution. The plane-parallel wall 11 which can in each case be seen on the right of the cuvette 10 does not act on the relative phase shifts, because of the different material distributions 8 and 9. As shown in FIG. 4(c), the cuvette 10 has two plane-parallel walls 11, with a solid body composed of the material 8 being placed on the inside of the wall 11, that is shown on the left here, in the central area of the phase filter 1. Despite the somewhat different configuration, the method of operation of this phase filter 1 corresponds to that shown in FIG. 4(a).

Figure 5:
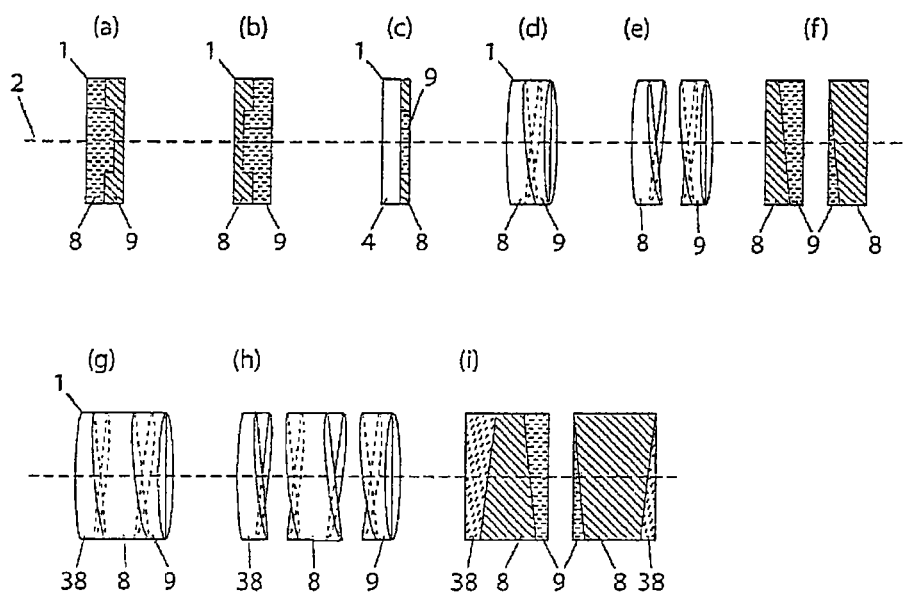
FIG. 5 shows three further embodiments of the wavelength-selective phase filter.

FIG. 5 illustrates five different further embodiments of the phase filter 1. In this case, the embodiments (a) and (b) in principle correspond to the embodiments of the cuvette 10 shown in FIGS. 4(a) and (b); however, in this case, both materials 8 and 9 are in the form of solid bodies. In contrast, in FIG. 5(c), the material 9 is provided only as the phase delay element 3 as shown in FIG. 1 in the central area of the phase filter 1, while the material 8 extends exclusively into its periphery. Both materials 8 and 9 are in this case arranged on a common substrate 4. The substrate 4 is neutral with respect to the aberration of the planar wavefronts, because of its plane-parallel boundary at right angles to the optical axis 2. The aberration of the planar wavefronts is in this case produced only by a refractive index difference $\Delta n$ between the materials 8 and 9 for the wavelength of the wavefronts to be distorted. For the wavefronts that are not to be distorted, the materials 8 and 9 in contrast have the same refractive indices n, because of the different dispersions characteristics $n(\lambda)$.

The embodiment of the phase filter 1 sketched in FIG. 5(d) differs from the embodiments shown in FIGS. 5(a)-(c) by the use of optical wedges instead of plane-parallel elements. The surfaces which bound the optical component are, however, also plane-parallel in this case. For the one light component, there is a refractive index difference $\Delta n$ between the materials 8 and 9 that are used, as a result of which two parallel linear phase ramps with gradients in opposite senses are applied to the wavefronts of the one light component, as it passes through. In contrast, the refractive indices of the materials 8 and 9 are identical for the other light component, as a result of which the wavefronts of the other light component are not changed by the element as they pass through. FIG. 5(e) shows the embodiment of the phase filter 1 as shown in FIG. 5(d) in the uncemented and separated state of the optical wedges. FIG. 5(f) shows a plan view of the boundary surfaces of the wedges which rest on one another in the case of the phase filter shown in FIG. 5(d), and illustrates the different configuration of the optical component on both sides of the optical axis 2.

Together with the co-authors, the inventors have already published a paper relating to the experimental implementation of the phase filter 1 shown in FIGS. 5(d)-(f), whose entire content is incorporated here by reference: D. Wildanger, J. Bückers, V. Westphal, S. W. Hell, L. Kastrup, "A STED microscope aligned by design". Opt. Exp. 17 (18), 16100-16110 (2009).

FIGS. 5(g)-(i) show a modification to the embodiment shown in FIGS. 5(d)-(f), based on three different materials 8, 9, 38. In the two areas which each apply a phase ramp to the one light component, the three materials 8, 9, 38 are arranged with two different wedge angles (one angle between the materials 38 and 8 and a different angle between the materials 8 and 9). The second material junction (and possibly even more materials with further wedge angles) make it possible to configure the profile of the overall dispersion curve in order, for example, to produce local plateaus in the dispersion curve, over which the phase shift, normalized with respect to the wavelength, of the one light component does not change with the wavelength. In addition, three or more materials can be used to ensure that the wavefront for the other light component remains constant as it passes through the element, if this is not possible using only two materials. The use of birefringent materials as one or more of these materials also opens up further degrees of freedom, for whose use, however, the two light components must also have different polarizations in addition to their different wavelengths.

The following text provides specific details relating to an optical component in the embodiment shown in FIGS. 5(g)-(i), using a circular aperture with a diameter of 5.6 mm for a linearly polarized light component at wavelengths in the range from 700 to 760 nm to produce a phase shift of the wavefronts with linear ramps from 0 to $\lambda/2$ and from $\lambda/2$ to $\lambda$ (discrepancies from the ideal between 700 and 760 nm: <2% of $\lambda$), and for a different light component with cross-polarization and with wavelengths in the range from 580 to 655 nm, to produce a constant phase shift of the wavefronts (discrepancies from the ideal of between 580 and 655 nm: <4% of λ):

Material 38: N-KZFS2 (Schott)
Material 8: MgF2, ordinary axis parallel to the polarization of the one light component
Material 9: S-BAL3 (Ohara Corp.)
Angle between 38 and 8: 3.9728°
Angle between 8 and 9: 3.7066°

Figure 6:
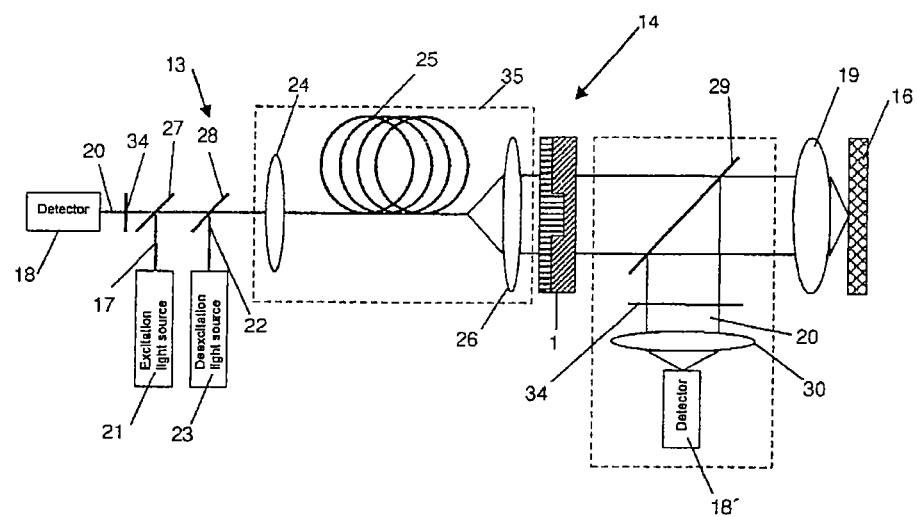
FIG. 6 shows the use of a wavelength-selective phase filter in an optical assembly of an STED fluorescence optical microscope, wherein two different positions of a detector are indicated for registration of fluorescence light which is emitted spontaneously from the sample.

FIG. 6 sketches an optical assembly 13 of an STED fluorescence optical microscope 14. The STED fluorescence optical microscope 14 is used for microscopic examination of a sample 16, in which case a fluorescence dye in the sample 16, used to mark structure of interest in the sample 16, is excited to fluoresce by means of excitation light 17, and the fluorescence light which is subsequently emitted spontaneously from the fluorescence dye is registered by a detector 18. In this case, the excitation light 17 is focused into the sample 16 by the same objective lens 19 as that which is also used to image the fluorescence light 20 from the sample 16 on the detector 18. In order to enhance the spatial resolution for imaging of the structure of interest in the sample on the basis of the registered fluorescence light 20, deexcitation light 22 from a laser as a deexcitation light source 23 is also used in addition to the excitation light 17 from a laser as the excitation light source 21. The deexcitation light 22 is likewise focused into the sample 16 by the objective lens 19. By selective wavefront aberration of the deexcitation light 22 with the wavelength-selective phase filter 1 the intensity of the deexcitation light 22 is not jointly focused with the excitation light 17 to the same focus point but due to interference the modified wavefronts of the deexcitation light 22 form an intensity null in the focus point. Since the phase filter 1 does not distort the excitation light 17, because of its different path length from that of the deexcitation light 22, the excitation light 17 can also pass through the phase filter 1. In the same way, the fluorescence light 20 may pass through the phase filter 1 and may be separated from the excitation light 17 and the deexcitation light 22 only after the phase filter 1. In the case of the assembly 13 shown in FIG. 6, the excitation light 17 and the deexcitation light 22 are jointly coupled via optics 24 into one end of a single-mode fiber 25, whose other end is arranged at the focal point of a lens 26, in order to form planar wavefronts both from the excitation light 17 and from the deexcitation light 22. The planar wavefronts of the excitation light 17 then continue as far as the objective lens 19, by which they are focused into the sample 16. In this case, they pass through the phase filter 1 without being deformed. In contrast, the planar wavefronts of the deexcitation light 22 are distorted in the desired manner by the phase filter 1. When it passes back from the sample 16, the fluorescent light 20 may remain uninfluenced by the phase filter 1, in the same way as the excitation light 17. However, it may also be distorted provided that at least a significant proportion enters the single-mode fiber 25 and arrives at the detector 18 behind the dichroic mirrors 27 and 28, which align the excitation light 17 from the excitation light source 21 and the deexcitation light 22 from the deexcitation light source 23 coaxially towards the lens 24. Alternatively, a detector 18' may also be arranged in such a way that a dichroic mirror 29 between the objective lens 19 and the phase filter 1 outputs the fluorescence light 20 to it, in which case a lens 30 which corresponds to the lens 26 is provided in order to focus the fluorescence light 20 onto the detector 18'. A fluorescence bandpass filter 34 or some other suitable device, such as a prism or grating with an aperture stop, is arranged in front of the detector 18 or 18' in order to allow only the fluorescence light to pass selectively through to the detector and to keep reflected components of the excitation light 17 or of the deexcitation light 22, or light at yet other wavelengths, away from the detector.

Figure 7:
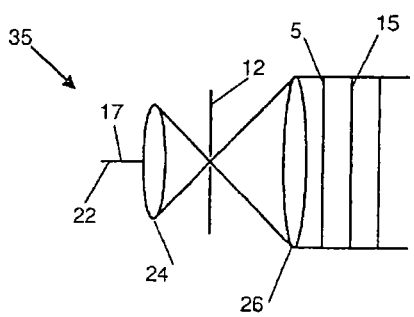
FIG. 7 shows a space filter with a pinhole as an alternative to a space filter, as used in the optical assembly shown in FIG. 6, with an optical waveguide.

FIG. 7 illustrates an alternative to an assembly 35 of the optical assembly 13 in FIG. 6, which is generally referred to as a spatial filter, and is used to form planar wavefronts 5, 15, which run parallel to one another, from the excitation light 17 and the deexcitation light 22. In this case, instead of the single-mode fiber 25, the opening of a pinhole 12 is arranged between the lenses 24 and 26, at their coincident focal points. The pinhole 12 is advantageous when no single-mode fiber 25 is available that is suitable for wavelengths of both the excitation light 17 and of the deexcitation light 22.

Many variations and modifications can be made to the preferred embodiments of the invention without departing from the spirit and principles of the invention. All such modifications and variations are intended to be included in the scope of the present invention as it is defined by the following patent claims.

LIST OF REFERENCE SYMBOLS

1 Phase filter
2 Optical axis
3 Phase delay element device
4 Substrate
5 Incident wavefront
6 Modified wavefront filter
7 Light
8 Material
9 Material
10 Cuvette splitter
11 Wall 38 Material
12 Pinhole
13 Optical assembly
14 STED fluorescence light microscope
15 Planar wavefront
16 Sample
17 Excitation light
18 Detector
19 Objective lens
20 Fluorescence light
21 Excitation light source
22 Deexcitation light
23 Deexcitation light source
24 Optics
25 Single-mode fiber
26 Lens
27 Dichroic mirror
28 Dichroic mirror
29 Dichroic mirror 30 Lens
34 Fluorescence bandpass
35 Spatial filter

We claim:
1. An optical assembly having:
a light source, which provides two optically different light components with essentially planar wavefronts on an optical axis, wherein the light components differ at least in their wavelength;
an objective lens, which projects the two optically different light components into a projection space; and
an optical component, which is arranged on the optical axis and has an aperture, through which the wavefronts of the two light components pass and, in mutually adjacent areas of the aperture, has a different structure along the optical axis with a different dispersion behavior n(λ), wherein both of the light components enter the optical component with essentially planar wavefronts, wherein the optical component causes phase shifts of the wavefronts of both of the light components, wherein the phase shift of the wavefronts of one light component has at least one step of at least one quarter of the wavelength of the one light component between the mutually adjacent areas of the aperture of different structure, and wherein the phase shift of the wavefronts of the other light component is constant as it passes through the optical component over the aperture, such that an intensity distribution of the one light component in the projection space by mutual interference differs from an intensity distribution of the other light component in the projection space.

2. The optical assembly as claimed in claim 1, wherein the phase shift of the wavefronts of the one light component has at least one step of at least 50% of the wavelength of the one light component between the mutually adjacent areas of the aperture of different structure.

3. The optical assembly as claimed in claim 1, wherein the phase shift of the wavefronts of the one light component has the at least one step in at least one direction which runs transversely with respect to the optical axis.

4. The optical assembly as claimed in claim 1, wherein the optical component is phase-corrected for the wavelength of the other light component over the aperture.

5. The optical assembly as claimed in claim 1, wherein the optical component is phase-correctable for the different wavelengths over the aperture.

6. The optical assembly as claimed in claim 1, wherein the objective lens focuses the two light components into a focus area, wherein the optical component causes different phase shifts of the wavefronts of the one light component such that the intensity distribution of that said one light component has a null at the center of the focus area at which the intensity distribution of the other light component is concentrated.

7. The optical assembly as claimed in claim 1, wherein the light which the objective lens collects from its focus area also passes through the optical component.

8. The optical assembly as claimed in claim 7, wherein the one light component and the other light component pass through a common light-forming component before the optical component, which said light-forming component is selected from the group comprising optical waveguides and pinholes, and wherein the light which is collected by the objective lens from its focus area likewise passes through the common light-forming component.

9. The optical assembly as claimed in claim 7, wherein the phase shift of the wavefronts of the one light component has the at least one step in all directions which run at right angles to the optical axis.

10. The optical assembly as claimed in claim 9, wherein the aperture of the optical component has a circular central area and a periphery which extends around it in an annular shape, between which the step in the phase shift of the one light component is 50% of its wavelength.

11. The optical assembly as claimed in claim 9, wherein the optical component causes a change in the phase shift of the one light component, which change increases in a circumferential direction around the optical axis, up to the wavelength of that said one light component.

12. The optical assembly as claimed in claim 1, wherein the one light component and the other light component pass through a common light-forming component before the optical component, which said light-forming component is selected from the group comprising optical waveguides and pinholes.

13. The optical assembly as claimed in claim 12, wherein the optical waveguide is a single-mode fiber.

14. The optical assembly as claimed in claim 1, wherein the optical component applies two linear phase ramps to the wavefronts of the one light component, said phase ramps are arranged parallel to one another in the aperture and have mutually opposite gradients of to 50%, and 50% to 100%, respectively, of the wavelength of that said one light component.

15. The optical assembly as claimed in claim 1, wherein the mutually adjacent areas with a different structure are each bounded in a direction of the optical axis by plane-parallel surfaces of the optical component.

16. The optical assembly as claimed in claim 15, wherein the entire optical component is bounded in a direction of the optical axis by two plane-parallel surfaces.

17. The optical assembly as claimed in claim 1, wherein the optical component has different materials in its mutually adjacent areas of different structure.

18. The optical assembly as claimed in claim 17, wherein at least one of the materials has a temperature-dependent dispersion behavior $n(\lambda, T)$, wherein a temperature control apparatus is associated with said at least one of the material.

19. The optical assembly as claimed in claim 17, wherein at least one of the materials has an electrically variable dispersion behavior $n(\lambda, U)$, wherein an electrode to which a voltage U can be applied is associated with said at least one of the material.

20. The optical assembly as claimed in claim 17, wherein at least one of the materials is selected from the group which comprises polymers, gels, immersion oils, dye solutions and liquid crystals.

21. The optical assembly as claimed in claim 1, wherein the optical component has the same materials of different thicknesses in its mutually adjacent areas of different structure.

22. The optical assembly as claimed in claim 21, wherein at least one of the materials has a temperature-dependent dispersion behavior $n(\lambda, T)$, wherein a temperature-control apparatus is associated with said at least one of the material.

23. The optical assembly as claimed in claim 21, wherein at least one of the materials has an electrically variable dispersion behavior $n(\lambda, U)$, wherein at least one electrode to which a voltage U can be applied is associated with said at least one of the material.

24. The optical assembly as claimed in claim 21, wherein at least one of the materials is selected from the group which comprises polymers, gels, immersion oils, dye solutions and liquid crystals.

25. The optical assembly as claimed in claim 21, wherein the optical component has a cuvette with an interior which holds one of the materials, wherein a length of the interior in the direction of the optical axis varies over the aperture of the optical component.

26. The optical assembly as claimed in claim 1, wherein the optical component is formed from plane-parallel optical wedges, both composed of at least two different optical materials, in two areas which are adjacent to one another transversely with respect to the optical axis.

27. The optical assembly as claimed in claim 1, wherein the light source provides the two optically different light components with essentially planar wavefronts on an optical axis, wherein the light components differ not only in their wavelength but also in their polarization, and wherein the optical component has at least one birefringent material.

* * * * *